United States Patent [19]

Achermann et al.

[11] 4,354,764
[45] Oct. 19, 1982

[54] SPECIMEN TESTING APPARATUS

[76] Inventors: Heinz Achermann, Sonnhaldenstrasse 2, CH-8610 Uster; Jürg Daetwyler, Bodenacherstrasse 105, CH-8121 Benglen, both of Switzerland

[21] Appl. No.: 221,023

[22] Filed: Dec. 29, 1980

[30] Foreign Application Priority Data

Jun. 13, 1980 [CH] Switzerland ............... 4568/80

[51] Int. Cl.³ ........................................... G01N 25/16
[52] U.S. Cl. ......................................... 374/56; 374/46; 73/805
[58] Field of Search ................ 73/15.6, 16, 805, 818, 73/826

[56] References Cited

U.S. PATENT DOCUMENTS

| | | | |
|---|---|---|---|
| 3,470,732 | 10/1969 | Welhoelter et al. | 73/15.6 |
| 3,474,658 | 10/1969 | Levy | 73/16 |
| 3,589,167 | 6/1971 | Hill | 73/16 |
| 4,235,114 | 11/1980 | Mohler | 73/826 |

Primary Examiner—Herbert Goldstein
Attorney, Agent, or Firm—Laubscher, Philpitt & Laubscher

[57] ABSTRACT

A specimen testing apparatus is disclosed, including a sensing device for engaging a specimen mounted on a support, an electrical measuring system associated with the sensing device for producing an electrical signal that is a function of a variation in a physical characteristic of the specimen as determined by the sensing device, and an electromagnetic compensation system for applying a compensating force to the sensing device. In one operating condition (as, for example, when the thermal expansion properties of the specimen are being tested), the compensation system is operable to apply to the sensing device a force compensating for the weight of the sensing device, thereby to cause the sensing device to rest upon the specimen in a weightless force-free manner. Alternately, the compensation system may be operable to apply to the sensing device a supplemental force in the compressive stressing condition, as might be desired when penetration tests are to be conducted on the specimen.

7 Claims, 1 Drawing Figure

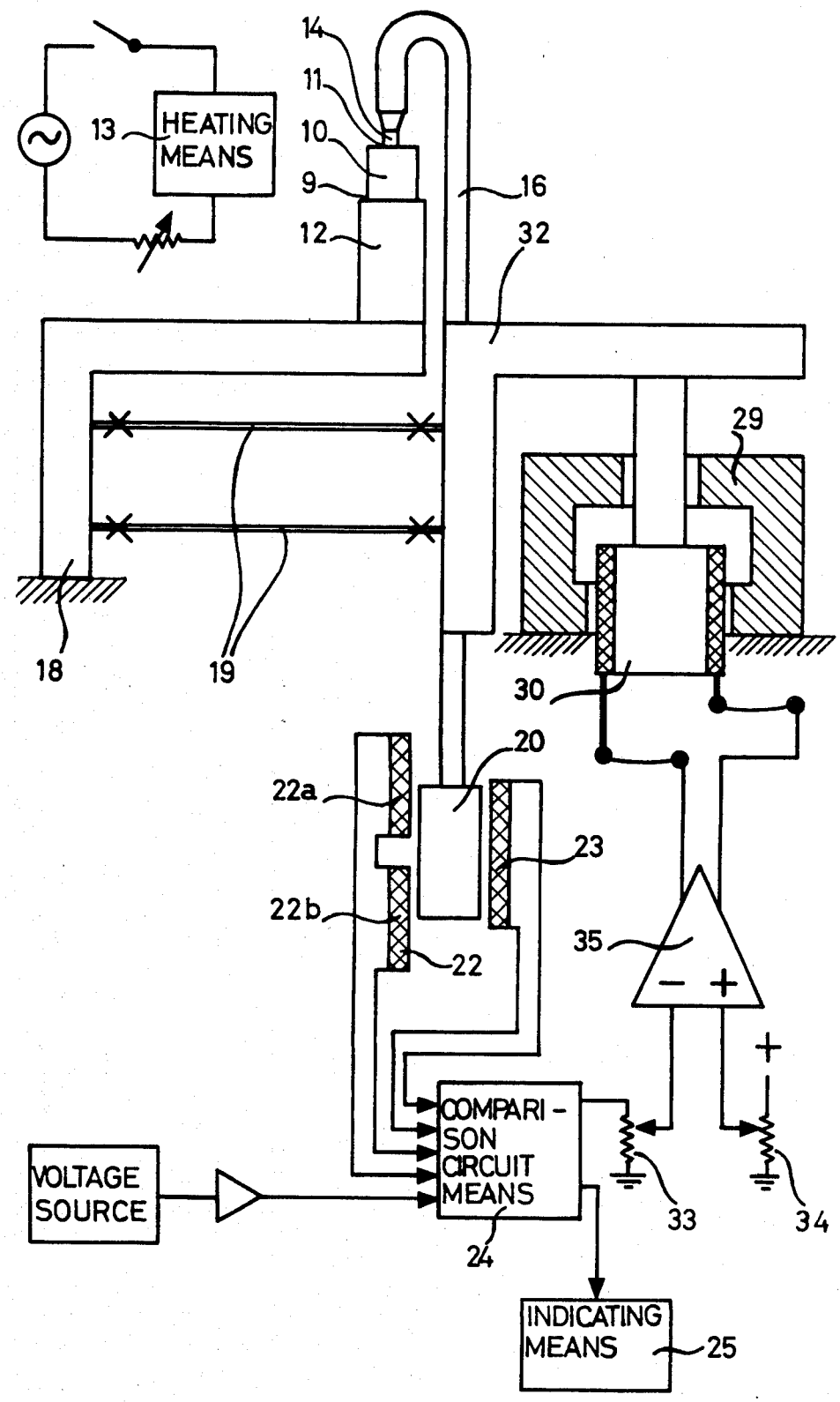

SPECIMEN TESTING APPARATUS

BRIEF DESCRIPTION OF THE PRIOR ART

This invention relates to an instrument for thermoanalytic measurement of a physical characteristic of a heatable specimen by means of a variably stressable measurement sensor device whose effect in terms of weight upon the specimen is influenced by an electromagnetic compensation system.

Instruments of this kind are known, for example, from U.S. Pat. No. 3,589,167. They are generally used in laboratories for research and control purposes and requirements for measurement accuracy are relatively high. They are used among other things to record thermally caused expansions of measurement specimens as well as for the determination of likewise thermally conditioned changes in the surface properties of coated and uncoated specimens.

These specimens are received in a specimen holder and can be heated, or cooled, if desired. The sensor head in a measurement sensor device monitors the position of the specimen's measurement surface which, due to the thermal influence, is displaced with respect to the fixed position of a reference surface, or it penetrates into the specimen which has become softer due to the effect of the heat.

To obtain a perfect measurement result, it is important that the inherent weight of the measurement sensor device be prevented from acting upon the specimen. Some instruments for this purpose contain compensation mechanisms, whereby the measurement sensor device is connected with buoyancy bodies which are submerged in a liquid tank. Such an arrangement contains several disadvantages. First of all, the instrument can be used only in a certain position. Secondly, all of the exchangeable measurement sensor devices—such as they are generally desired for the purpose of adjustment to the particular measurement variants—must have the same weight, or the buoyancy bodies must be made in a more or less submersible manner, and this, of course, leads to laborious and awkward designs.

It is also possible, for the purpose of compensating for the inherent weight of the measurement sensor device, to provide spring-activated means which, however, in view of the required measurement accuracy, are impractical on account of their inherent disadvantages, but above all because of their distance-dependent effect.

In certain measurements, such as determining the surface hardness of a specimen, it may be desirable to place the sensor of the measurement sensor device upon the specimen with a certain controllable force. This is achieved by connecting a receiving surface for weights with the measurement sensor device. The weights here are manually placed upon the receiving surface as required. But mistakes were made very often and they invalidated the measurement results; moreover, it is not possible to stress the measurement sensor device steplessly and during one measurement operation in a variable fashion.

Another essential disadvantage of known specimen testing instruments resides in the fact that the bracing of the measurement sensor device is accompished laterally with respect to the direction of movement of the sensor by means of customary bearings. These known bearings possess comparatively high adhesion for sliding friction, and thus they impaired the measurement results.

The purpose of the invention thus is to create an instrument of the kind described initially which will not contain the disadvantages mentioned above, and which, in addition to easier handling, will achieve greater measurement result accuracy.

SUMMARY OF THE INVENTION

Accordingly, a primary object of the present invention is to provide a specimen testing apparatus including electromagnetic compensation means for applying to the specimen sensing means a conrollable force. In one embodiment, as for example when the thermal expansion properties of a specimen are being tested, the compensation force is of a magnitude and direction to cause the sensor head of the sensing means to engage the upper surface of the specimen in a weightless manner. In another embodiment, as for example, when the penetrability or hardness of the specimen is to be tested, the compensation force applied to the sensing means is in the specimen compressive stressing direction, whereby the sensing head is pressed against the specimen surface with a predetermined force (supplementing the normal weight of the sensing device).

According to an important advantage of the invention, the force with which the sensor head of the measurement sensor device is pressed against or into the measurement surface of the specimen, or the way in which a clamped specimen can be subjected to a tensile stressing force, can be selected steplessly fro zero on up, independently of the weight of the measurement sensor device and of the measurement distance. It is thus possible in a simple manner to compensate for the weight of the measurement sensor device and to perform a force-free measurement, or to stress the sensor with a certain force in that the weight of the measurement sensor device is compensated only partly or not at all, or in that, in addition to the weight of the measurement sensor device, another force can be exerted.

As a consequence of the invention, the use of spring means for effecting the desired compensation is avoided, as well as the use of buoyant bodies and liquid containers; also, the use of manipulatable weights is eliminated, whereby the possibility of error is avoided. Operation is simplified considerably and the instrument can be so designed that it can assume any desired position in space, in other words, for example, it can also work horizontally.

According to another feature of the invention, the specimen sensing mechanism is guided for displacement relative to the fixed specimen support means by resilient parallelogram guide means, and since the use of customary bearings has been eliminated, the developing friction forces are considerably reduced and the measurement accuracy thus is considerably improved. Moreover, the spring forces of the resilient guide bearings are easily compensated for by the electromagnetic compensation force.

BRIEF DESCRIPTION OF THE DRAWING

Other objects and advantages of the inventions will become apparent from a study of the following specification when viewed in the light of the accompanying drawing, the single FIGURE of which is a diagrammatic partly sectioned view of the specimen testing apparatus of the present invention.

DETAILED DESCRIPTION

Referring now to the drawing, the specimen measuring apparatus includes a specimen holder 12 having a fixed reference surface 9 upon which is supported a specimen 10 having an upper measurement surface 11. Heating means 13 are provided for heating the specimen to a desired temperature.

In accordance with the present invention, vertically displaceable measurement sensing means 16 are provided including a sensor head 14 arranged for engagement with the upper measurement surface 11 of the specimen 10. The sensor head 14 is adapted either to follow the vertical displacement of the specimen upper surface 11 relative to the fixed surface 9 (as produced, for example, by the expansion of the specimen resulting from the heating thereof by heating means 13), or to penetrate somewhat into the specimen surface 11 (for example, during a surface hardness test by a sharp sensor head 14, wherein a compressive load is applied to the specimen by the measurement sensing means 16). The sensor head 14, the specimen holder 12, and/or the measurement sensor device 16 are designed to be interchangeable with like components for adaptation to varios specimens and various measurement requirements.

The measurement sensing means 16 is guided for vertical movement relative to the fixed specimen support means 18 by parallelogram spring guide means including a pair of resilient guide links 19. Connected with the measurement sensing means is a ferromagnetic body 20 arranged for displacement between a pair of stationary coil means 22 and 23, the coil 22 having a pair of series-connected physically separated coil sections 22a and 22b. The coils 22 and 23 are connected with the signal comparison means 24 of a signal measuring and indicating circuit which is operable to generate a sensor displacement signal as a function of the displacement of the ferromagnetic body 20 relative to the stationary coils 22 and 23, which signal is read by indicating means 25. If desired, the body 20 connected with the sensor measuring means 16 may be permanently magnetized.

OPERATION

In operation, assume that the specimen 10 is formed of a material that will expand when heated, thereby increasing the distance between the specimen upper surface 11 and the fixed support surface 9. Consequently, sensor head 14 and sensor measurement means 16 are shifted upwardly against the restoring biasing force of the resilient parallelogram guide means 19. Owing to the resulting displacement of ferromagnetic body 20 relative to the stationary coils 22 and 23, an electrical signal is generated that is a function of the amount of vertical displacement of the ferromagnetic body 20 (and, consequently, the displacement of sensor 14 relative to the fixed surface 9), which signal generated by the comparison circuit means is read by the indicating means 25. Thus, the extent of expansion of specimen 10 upon the application of heat is converted into an electrical signal of corresponding magnitude that is read off indicating means 25 for analysis.

In an instrument in keeping with the above description, assume that specimen 10 is stressed in compression by sensor head 14 owing to the inherent weight of the measurement sensor device 16. In order to get exact measurement results, it may be necessary to measure without any force to the greatest possible extent, that is to say, it may be necessary to have sensor head 14 rest against measurement surface 11 without being stressed, or, in other words, to compensate for the inherent weight of the measurement sensor device 16. In other kinds of measurements of the type directed to measurement of the penetration depth of the sensor head 14 into measurement surface 11, it may also be necessary to stress sensor head 14 with a certain force which likewise changes in terms of time but which generally, of course, does not correspond to the weight of the measurement sensor device 16 but rather can be larger or smaller than it. To compensate for the inherent weight of the measurement sensor device 16 or to generate a force acting through the sensor head 14 upon the measurement surface 11, the following steps are taken.

Another coil arrangement including compensation coil 30 is connected with measurement sensor device 16 by means of mechanical connection or arm 32. This coil arrangement 30 is in a magnetic field which can be generated by stationary permanent magnet means 29 or by a similar electromagnetic mechanism. The ends of compensation coil 30 are connected with the output terminals of differential amplifier 35 one input terminal of which is connected with the output terminal of comparison circuit means 24 via potentiometer 33, and the other input terminal of which is connected with variable potentiometer 34.

In operation, upon the application of a voltage to the coil arrangement 30, the later will be subjected to a force extending in the direction of its longitudinal axis. Through connecting arm 32, this force is transmitted to the measurement sensor device 16, thereby changing the force by means of which sensor 15 acts upon measurement surface 11. In order to get a reasonably force-free expansion measurement, the voltage for the coil arrangement 30 must be so selected that the inherent weight of the measurement sensor device 16 will be cancelled out by a force extending in the direction opposite to gravity. The restoring forces of resilient guide bearings 18 are likewise compensated for on the basis of the deflection of the measurement sensor device 16 with the aid of the measurement signal from comparison circuit 24, regulator 33, and compensation coil arrangement 30.

If, on the other hand, a measurement is supposed to determine the penetration depth of sensor head 14 into specimen 10, this voltage must be so selected that this inherent weight will be compensated for only partly or not at all, or that, in addition to the inherent weight of the measurement sensor device, a force, acting in the same direction as the inherent weight, will be exerted upon the measurement surface via the sensor.

It is thus possible in a simple manner and with a single device not only to compensate for the inherent weight of the measurement sensor device either entirely or partly, but also to generate an additional force in addition to the inherent weight. Here the particular required force values can be selected in advance by adjusting the potentiometer 34 so that the current intensity, which is in effect in each case in compensation coil arrangement 30, will be made up of the preselected portion and the portion determined by potentiometer 33.

By means of the corresponding adjustment of potentiometer 34, the current intensity can be so dimensioned that, when it is desired to change specimens, measurement sensor 14 will be lifted off the measurement surface 11.

It should be mentioned that, if desired, a microcomputer can be used for a preselection of the force values: after numerical input of the desired values, the latter will then selected the potentiometer or corresponding current stages.

By reversing the arrangement of the specimen and the measurement sensor whereupon the sensor will apply tensile stress to the specimen, whereby compression of the specimen can also be measured (for example, in the case of shrinkage hoses).

By means of the instrument according to the present invention, one can perform various thermomechanical measurements as a function of the temperature and/or the time. For example, measurements may be made under a predetermined bearing load (without adhesion friction), in other words, measurements of the changes in length at constant force, from which, for example, one can derive the expansion coefficient of the specimen.

Moreover, measurements of length changes may be made by a force which changes either just once or in a cyclic fashion, for example, with frequencies between 0.1 and 1 Hz, from which, for example, the elasticity of the specimen can be determined.

Measurements of surface properties of the specimen may also be made, for example, softening upon the application of heat.

In addition to measurements made during variations of temperature, one can also make measurements under isothermal conditions if, for example, the expansion behavior is to be investigated under certain environmental test conditions (for example, under varying conditions of humidity).

While the preferred forms and embodiments of the invention have been illustrated and described, it will be apparent that various other changes and modifications may be made without deviating from the inventive concepts set forth above.

What is claimed is:

1. Specimen testing apparatus comprising
(a) specimen support means (12) for supporting a specimen (10);
(b) specimen sensing means (16);
(c) guide means (19) connecting said sensing means for displacement relative to said support means, said guide means comprising a parallelogram arrangement including a pair of parallel resilient guide links (19) normally biasing said sensing means toward an initial position in engagement with a specimen on said support, whereby variation of a given physical characteristic of the specimen produces a corresponding displacement of said sensing means relative to said support means;
(c) means (22, 23, 24) for generating an electrical signal as a function of the displacement of said sensing means from said initial position; and
(d) electromagnetic compensation means (29, 30) for applying to said specimen sensing means a force tending to displace the sensing means relative to said support means.

2. Apparatus as defined in claim 1, wherein said specimen sensing means includes a sensor head (14) adapted to engage the upper surface of the specimen.

3. Apparatus as defined in claim 2, wherein said compensation means is operable to apply to said sensing means an upward force of such a magnitude and direction as to cause said sensor head to engage the specimen surface in a weight-free stressless manner when said sensing means is in its initial condition.

4. Apparatus as defined in claim 2, wherein said compensation means is operable to apply to said sensing means a downwardly directed force supplementing the weight force applied to the specimen by said sensing means.

5. Apparatus as defined in claim 1, and further including heating means 13 adjacent the specimen support means for heating the specimen.

6. Apparatus as defined in claim 1, wherein said electrical signal generating means comprises coil means (22, 23) connected with the specimen support means adjacent said sensing means, and a ferromagnetic member (20) connected with said specimen sensing means.

7. Apparatus as efinedin claim 6, wherein said compensation means includes a ferromagnetic member (29) connected with said support means, and a coil (30) mounted on said sensing means, said coil being electrically connected with said signal generating means.

* * * * *